US006556857B1

(12) United States Patent
Estes et al.

(10) Patent No.: US 6,556,857 B1
(45) Date of Patent: Apr. 29, 2003

(54) ROTATION LOCKING DRIVER FOR IMAGE GUIDED INSTRUMENTS

(75) Inventors: Bradley T. Estes, Memphis, TN (US); Douglas N. Baker, Rancho Santa Margarita, CA (US)

(73) Assignee: SDGI Holdings, Inc., Wilmington, DE (US)

( * ) Notice: Subject to any disclaimer, the term of this patent is extended or adjusted under 35 U.S.C. 154(b) by 262 days.

(21) Appl. No.: 09/695,125

(22) Filed: Oct. 24, 2000

(51) Int. Cl.$^7$ .................................................. A61B 5/05
(52) U.S. Cl. ........................ 600/424; 600/428; 600/434
(58) Field of Search ................................ 600/424, 425, 600/427, 428, 433, 434, 435

(56) References Cited

U.S. PATENT DOCUMENTS

| | | | |
|---|---|---|---|
| 5,499,632 A | * 3/1996 | Hill, III et al. | 600/434 |
| 5,518,164 A | * 5/1996 | Hooven | 600/104 |
| 5,549,108 A | * 8/1996 | Edwards et al. | 607/122 |
| 5,577,654 A | * 11/1996 | Bishop | 600/137 |
| 5,718,239 A | * 2/1998 | Newby et al. | 600/576 |
| 5,749,835 A | * 5/1998 | Glantz | 600/424 |
| 6,021,343 A | 2/2000 | Foley et al. | 600/429 |
| 6,079,681 A | 6/2000 | Stern et al. | 248/278.1 |

FOREIGN PATENT DOCUMENTS

WO          WO 96/11624          4/1996

* cited by examiner

Primary Examiner—Philip H. Leung
(74) Attorney, Agent, or Firm—Woodard, Emhardt, Naughton Moriarty & McNett LLP (57) ABSTRACT

A trackable medical instrument includes a guide member and an emitter array coupled to the guide member. A drive shaft is rotatably coupled to the guide member, and a locking mechanism is provided along the drive shaft. The emitter array emits a signal that is used to track the position of the guide member. The locking mechanism has an unlocked position in which the drive shaft rotates relative to the guide member. The locking mechanism also has a locked position in which the drive shaft is rotationally stationary relative to the guide member. A processor tracks medical instruments using a sensor array and a reference array. A display that is operatively coupled to the processor displays the position of the instrument in relation to a patient.

19 Claims, 9 Drawing Sheets

ROTATION LOCKING DRIVER FOR IMAGE GUIDED INSTRUMENTS

BACKGROUND OF THE INVENTION

The present invention generally relates to computer assisted medical navigation systems, and more specifically, but not exclusively, concerns a trackable medical instrument that is rotationally lockable.

Computer assisted medical navigation systems aid in guiding medical instruments within a patient during surgery. With such systems, images of the body of the patient are taken with an imaging device, such as a CAT scanner (Computerized Axial Tomography scanner). The medical instrument has a tool that is attached to a guide member, and a tracking device is attached to the medical instrument so that the tool can be tracked by the system. The surgeon positions the instrument by viewing on a display the relative position of the tool within the patient in order to avoid damaging organs. Generally, the longitudinal position of the tool is fixed so that the exact position of the tool can be determined. With some medical instruments that rotate during use, such as drills, a surgeon using the system cannot determine the exact orientation of the instrument during surgery. Serious injury to the patient can occur if the tool is unexpectedly rotated or oriented at the wrong position during surgery. Therefore, there is a need in the art for a medical navigation system that is simple to use and that can precisely locate the orientation of a rotatable surgical instrument.

SUMMARY OF THE INVENTION

One form of the present invention is directed to a unique trackable medical instrument. The medical instrument includes a guide member and emitter coupled to the guide member. The emitter array is used to track the position of the guide member. A drive shaft is rotatably coupled to the guide member, and a locking mechanism is provided along the drive shaft. The locking mechanism has an unlocked position in which the drive shaft rotates relative to the guide member, and the locking mechanism has a locked position in which the drive shaft is rotationally stationary relative to the guide member.

DESCRIPTION OF SELECTED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the art that some of the features which are not relevant to the invention may not be shown for the sake of clarity.

Figure 1:
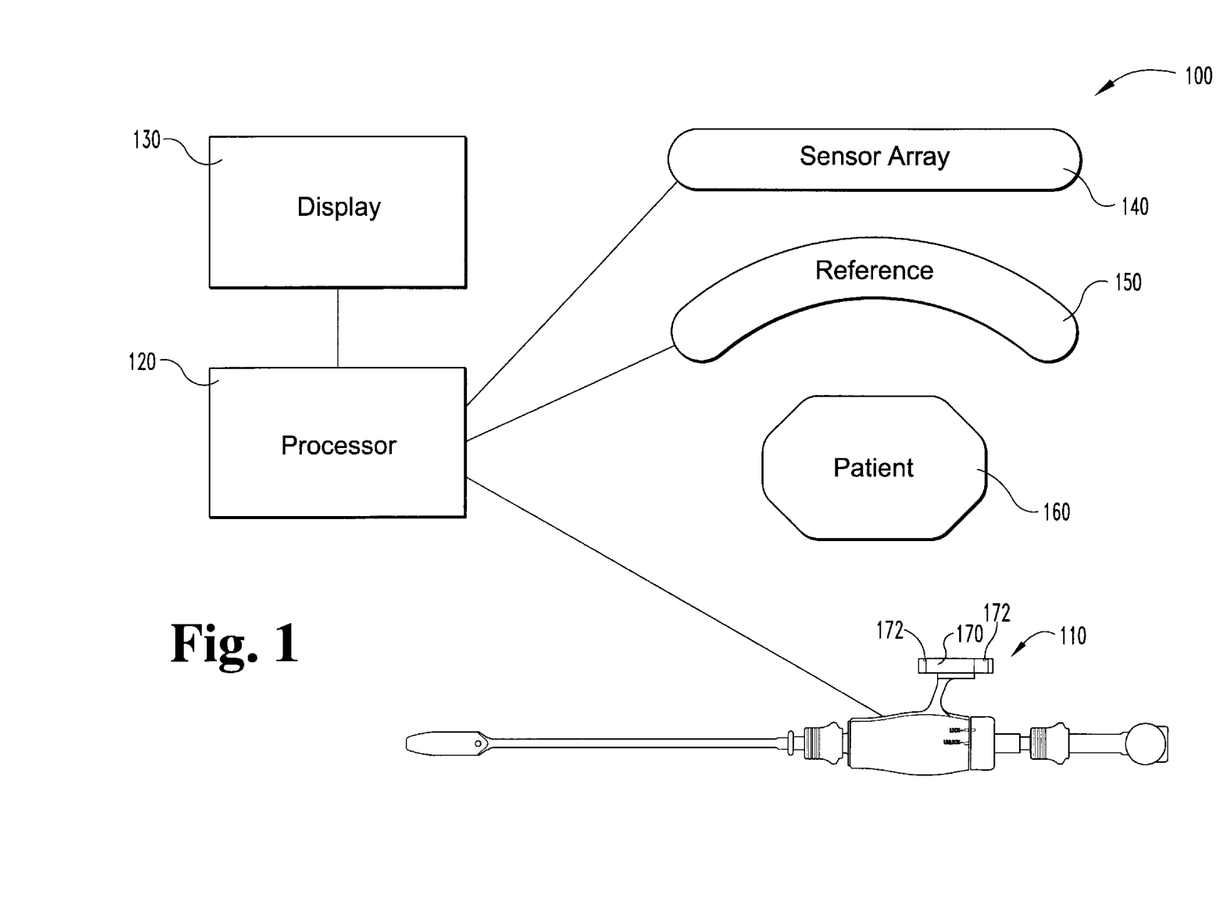
FIG. 1 is a schematic view of a computer assisted image guided system having a trackable medical instruments according to one embodiment of the present invention.

A surgical navigation system 100 is shown in a schematic form in FIG. 1. A trackable medical instrument 110 according to one embodiment of the present can be used in conjunction with a wide variety of surgical navigation systems, such as the system 100 shown in FIG. 1. A more detailed description of such types of systems are disclosed in PCT Application Ser. No. PCT/US/95/12984 (Publication No. WO/96/11624) to Buchholz et al., and U.S. Pat. No. 6,021,343 to Foley et al., which are hereby incorporated by reference. It should be understood that the trackable medical instrument 110 according to the present invention can be used in other generally known surgical navigation systems besides the one described herein.

The system 100 includes a processor 120 operatively coupled to the instrument 110, and a display 130 operatively coupled to the processor 120. A sensor array 140 is operatively coupled to the processor 120. A reference array 150 is operatively coupled to the processor 120, and the reference frame 150 is spatially fixed along a patient 160. A trackable emitter array 170 having a plurality of emitters 172 is coupled to instrument 110. The emitters 172 in one particular embodiment include light emitting diodes (LED's). It should be appreciated that the emitters 172 can include other types of tracking devices generally known by those skilled in the art.

The emitters 172 in the trackable emitter array 170 emit signals corresponding to the position of the instrument 110 during surgery. The reference array 150 generates signals representing various reference body locations of the patient 160. The sensor array 140 receives the signals sent from the reference array 150 and the emitter array 170, and the processor 120 triangulates the position of the medical instrument 110 based on these signals. After the processor 120 triangulates the position, the display 130 displays the relative location of the medical instrument 110 within the patient 160.

Figure 2:
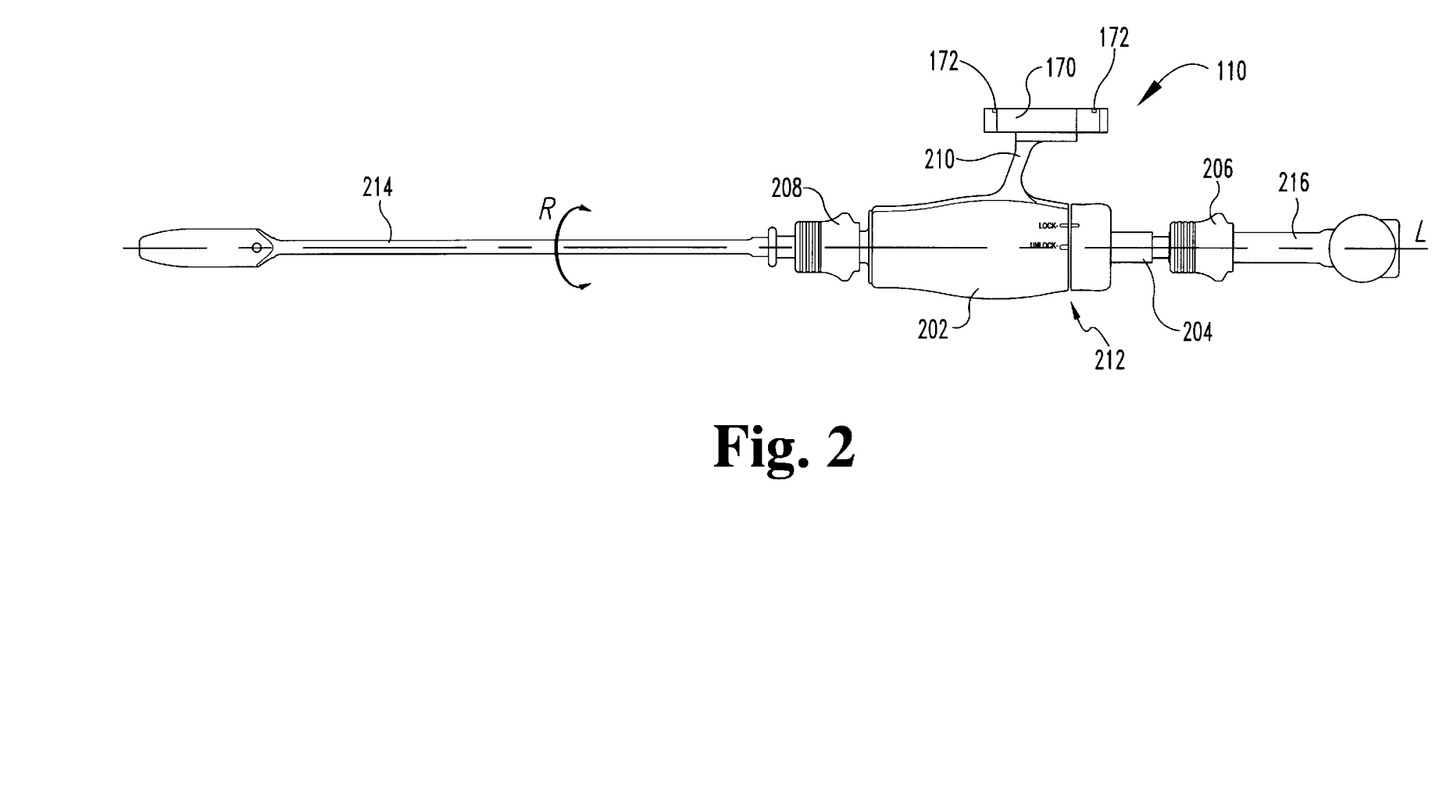
FIG. 2 is a side view of the medical instrument shown in FIG. 1.

As shown in further detail in FIG. 2, the instrument 110 includes a guide member 202. A drive shaft 204 is rotatably coupled to the guide member 202 and has ends extending from both ends of the guide member 202. The drive shaft 204 is rotatable in directions R relative to the guide member 202 and is fixed relative to the guide member 202 along a longitudinal axis L of the shaft 204. A quick connect drive-coupling member 206 is provided at one end of the drive shaft 204, and a quick connect tool-coupling member 208 is provided at the other end of the drive shaft 204.

The guide member 202 further includes a tracking platform 210 on which the emitter array 170 is slidably coupled. The instrument 110 has a locking mechanism 212 provided along the drive shaft 204. In the illustrated embodiment, the locking mechanism 212 is located between the guide member 202 and the drive-coupling member 206 so that the locking mechanism 212 can be easily actuated during surgery. It should be appreciated, however, that the locking mechanism 202 can be located at other locations along the drive shaft 204.

A driver member 216 is coupled to the drive-coupling member 206. The drive-coupling member 206 is adapted to quickly connect and disconnect the drive member 216 from the drive shaft 204. In the illustrated embodiment, the drive 216 is a manually driven handle. The drive 216 can also include other types of drives generally known by those skilled in the art, such as a mechanically driven shaft. A tool 214, such as a drill bit or awl, is coupled to quick connect tool-coupling member 208. The tool-coupling member 208 is adapted to quickly connect and disconnect the tool 214 from the drive shaft 204. It should be understood that the tool 214 can include other types of tools generally known by those skilled in the art.

Figure 3:
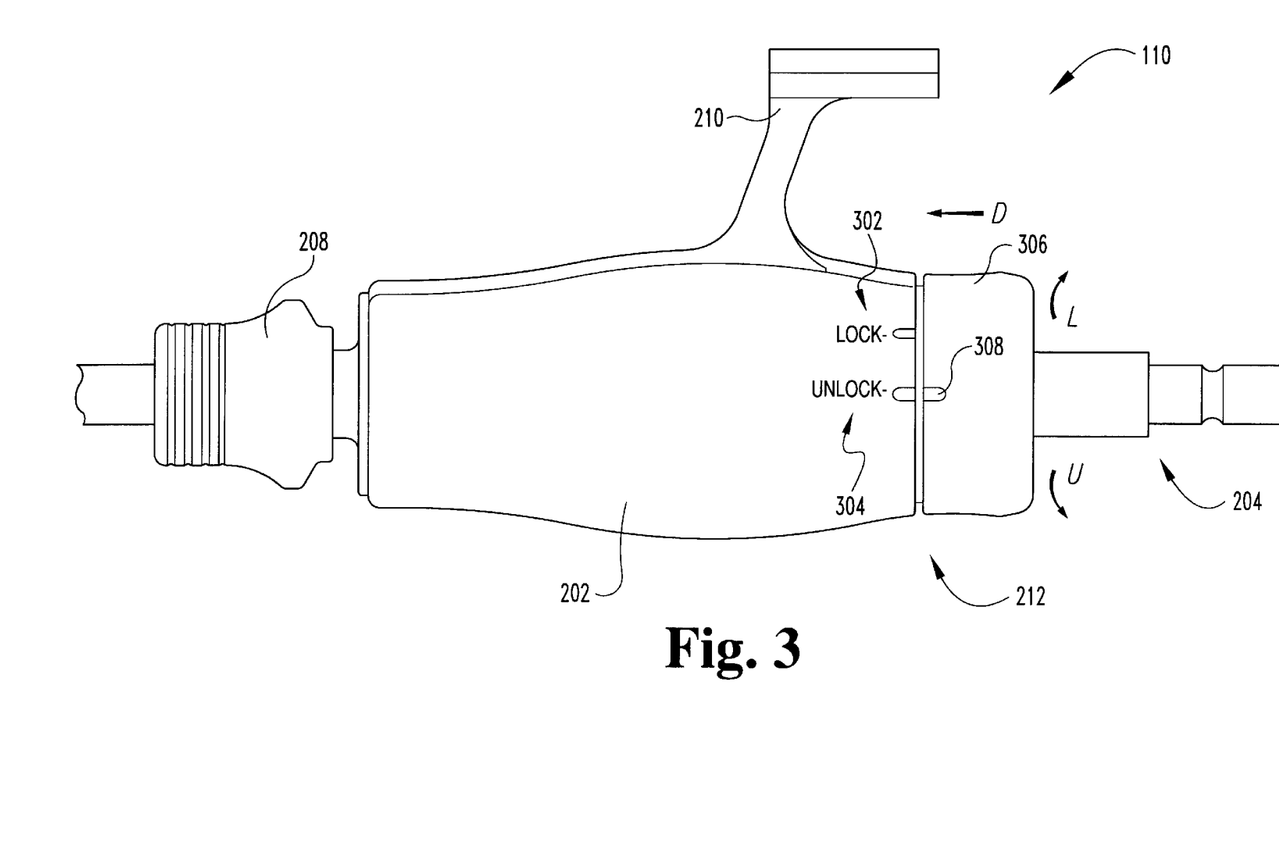
FIG. 3 is an enlarged view of the medical instrument shown in FIG. 1 with a locking mechanism in an unlocked position.

An enlarged view of the instrument 110 with the locking mechanism 212 in an unlocked position is shown in FIG. 3. As illustrated, the locking mechanism 212 includes a locked position indicator 302 and an unlocked position indicator 304. The locking mechanism 212 further includes a cylindrically shaped cover 306 that has a position indicator 308 defined thereon. The position indicator 308 aligns with the locked and unlocked position indicators 302 and 304 in order to indicate the status of the locking mechanism 212.

When the locking mechanism 212 is in the unlocked position, the drive 216 can be freely rotated in order to rotate the drive shaft 204. This rotation of the drive shaft 204 in turn rotates the tool 214. In order to unlock the locking mechanism 212, the cover 306 is pushed in direction D towards the guide member 202 and rotated in direction U into the unlocked position, which is indicated by the unlocked position indicator 304. To lock the locking mechanism 212, the cover 306 is pushed in direction D and rotated in direction L into the locked position as indicated by the locked position indicator 302. When the shaft 204 is rotationally locked by the locking mechanism 212, the drive shaft 204 and the tool 214 can not be rotated relative to the guide member 202. More importantly, the locking mechanism 212 locks the shaft 204 and the tool 214 in a specified orientation with respect to the emitter array 170 and the guide member 202. This ensures that a surgeon knows the exact orientation of the tool 214 within the patient.

Figure 4:
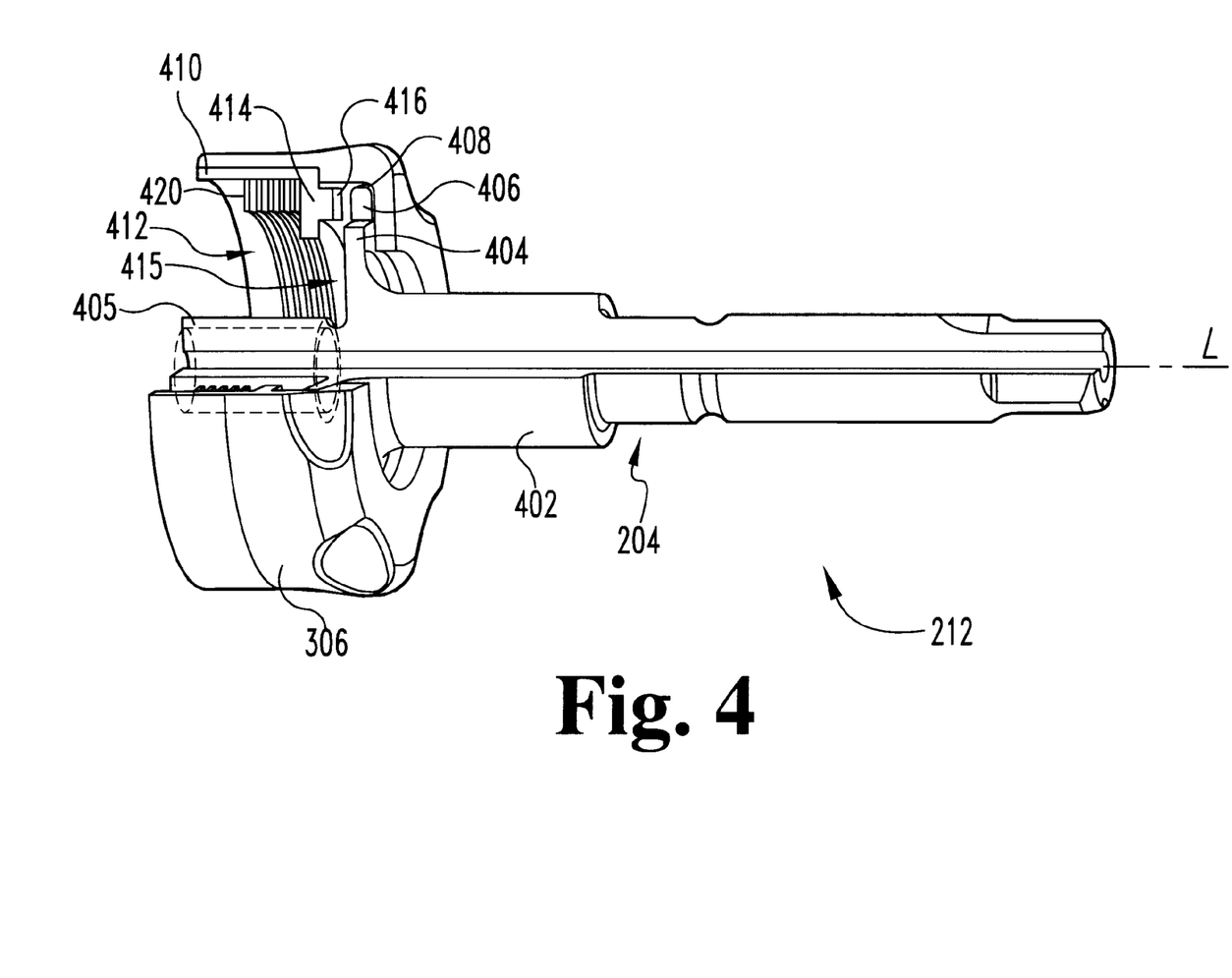
FIG. 4 is a cross-sectional perspective view of the locking mechanism in the unlocked position.
Figure 5:
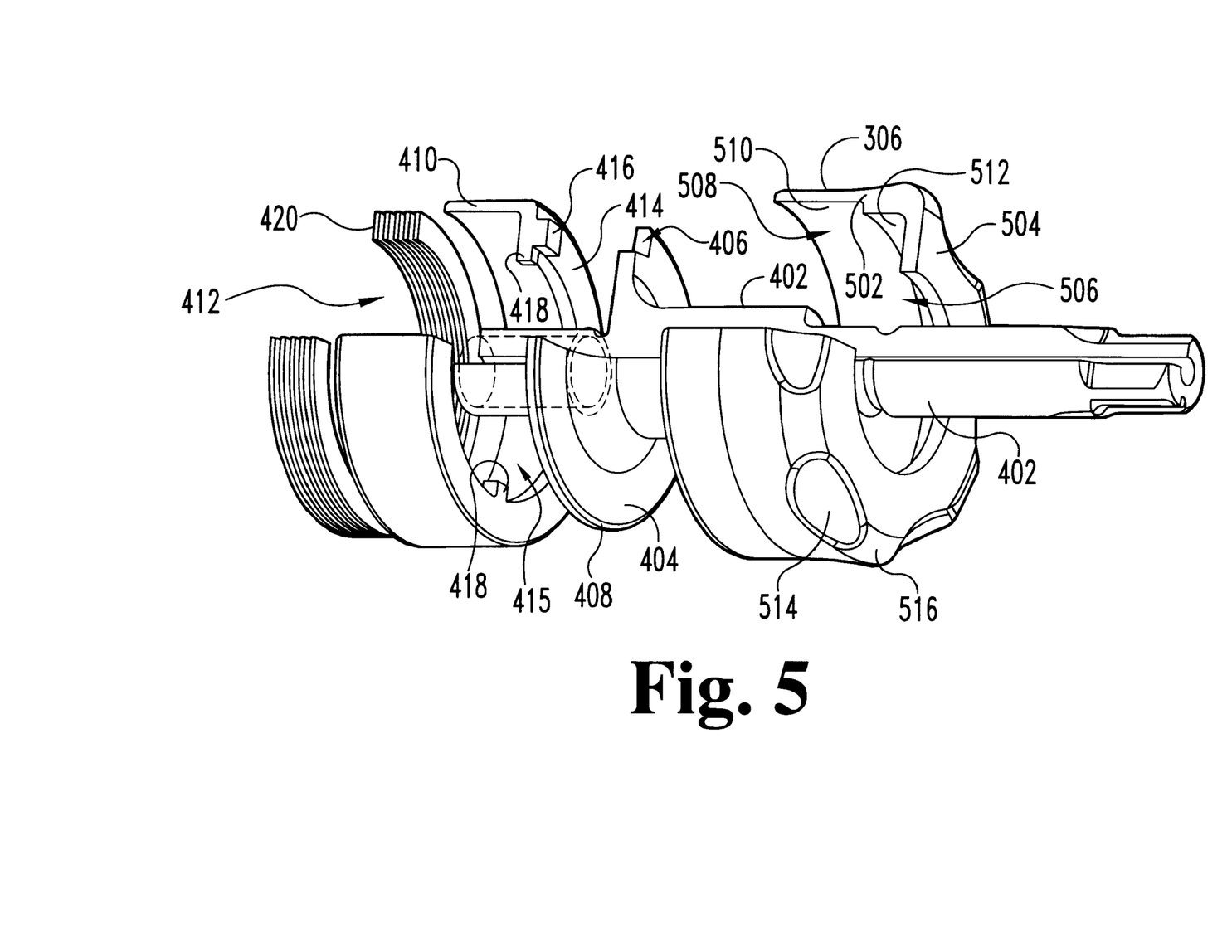
FIG. 5 is an exploded cross-sectional perspective view of the locking mechanism.
Figure 6:
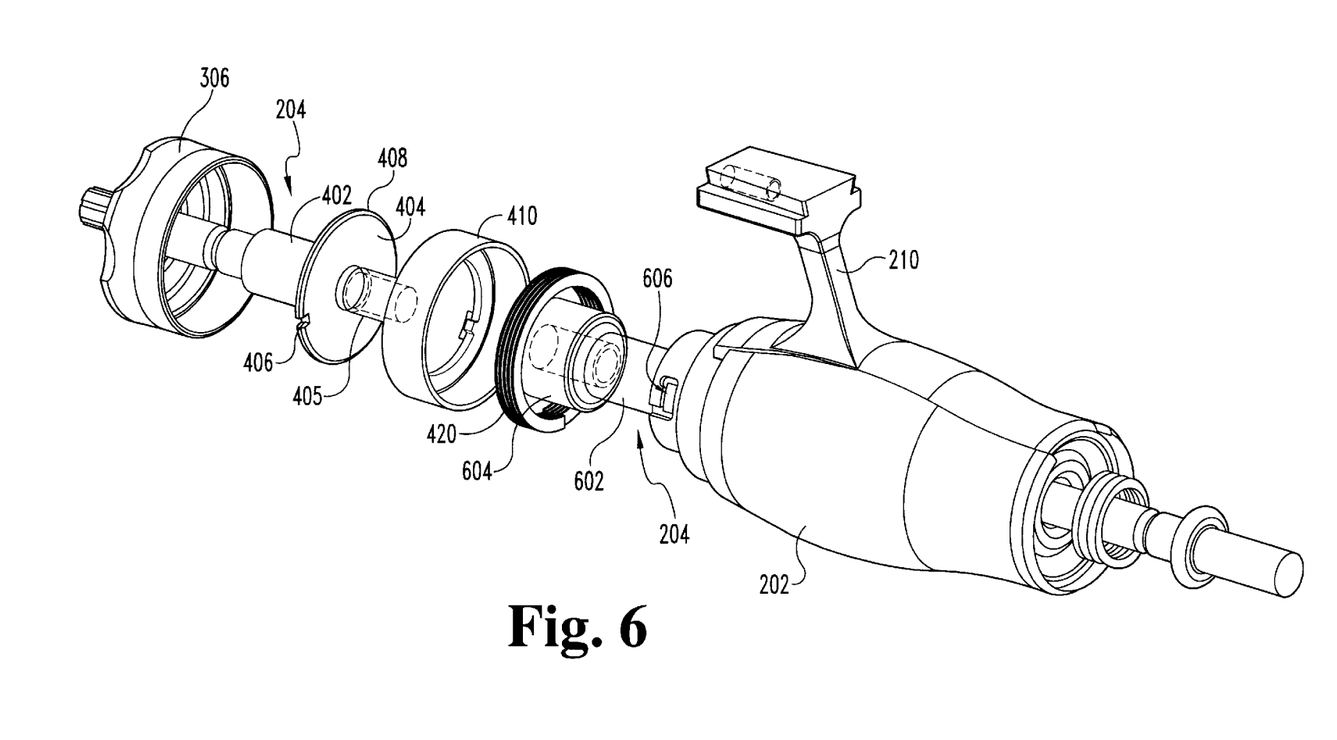
FIG. 6 is an exploded view of the medical instrument shown in FIG. 1.

The locking mechanism 212 is in the unlocked position in FIG. 4. The drive shaft 204 includes a retaining shaft portion 402 with a circular retention flange 404 and a connection portion 405. The retention flange 404 has a locking slot 406 defined in an outer peripheral portion 408 of the retention flange 404. As illustrated in FIGS. 4–6, a cylindrical locking member 410 is provided along the drive shaft 204 between the retention flange 404 and the guide member 202. The locking member 410 has a cylindrical cavity 412 through which the retaining shaft portion 402 of the drive shaft 204 passes. The locking member 410 further has a radially inward extending flange 414 at an end adjacent to the retention flange 404 of the retaining shaft 402. The inward extending flange 414 has an opening 415 defined therein that communicates with the cylindrical cavity 412. The inward extending flange 414 extends inwards such that the inward extending flange 414 overlaps with the retention flange 404 of the retaining shaft 402. The inward extending flange 414 has a locking pin 416 and a guide pin 418 extending therefrom. The locking pin 416 extends towards the retention flange 404 of the retaining shaft 402, and the guide pin 418 extends within the opening 415 towards the longitudinal axis L of the drive shaft 204.

A coil spring 420 is provided within the cavity 412 between the inward flange 414 of the locking member 410 and the guide member 202. The cover 306 is snuggly fitted around the locking member 410. As illustrated in FIG. 5, the cover 306 has a cylindrical body portion 502 and an end flange 504. The end flange 504 defines an opening 506 through which the retaining shaft 402 passes. The end flange 504 of the cover 306 overlaps with the retention flange 404 of the retaining shaft 402. The end flange 504 and the body portion 502 of the cover 306 define a locking member cavity 508 in which the locking member 410 is fitted. The body portion 502 has a locking member engagement portion 510 in which the locking member 410 is fitted. The body portion 502 further has a flange enclosure portion 512 in which the retention flange 404 of the retaining shaft 402 is enclosed between the end flange 504 of the cover 306 and the inward extending flange 414 of the locking member 410.

As shown in FIG. 6, the shaft 204 further includes a guide member shaft 602 with a retaining shaft connector 604. The connection portion 405 of the retaining shaft 402 is rotationally fixed to the connector 604 of the guide member shaft 602. In one embodiment, the connection portion 405 is press fitted to the connector 604. The guide member 202 further has a guide slot 606 in which the guide pin 418 slides.

Figure 7:
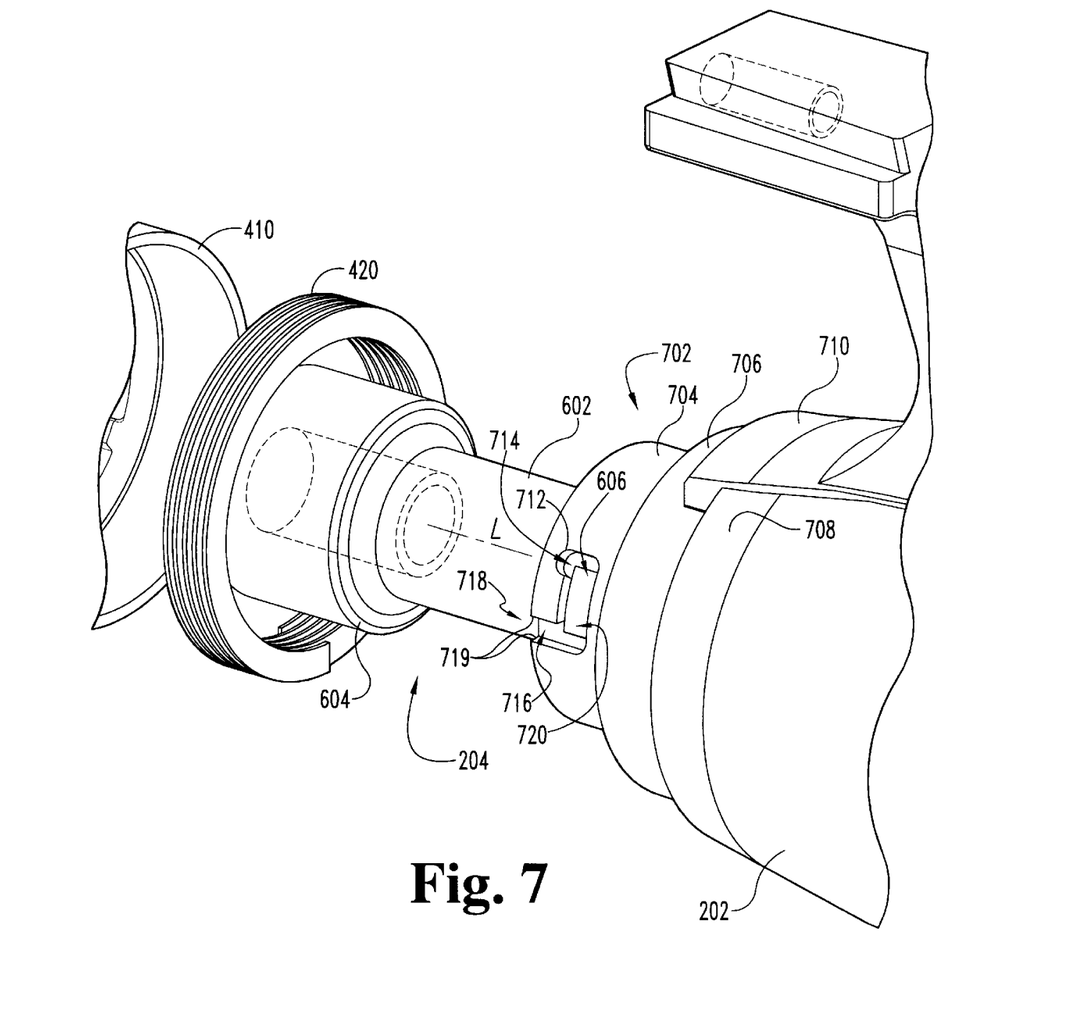
FIG. 7 is an enlarged view of a portion of the view shown in FIG. 6.

As illustrated in FIG. 7, the guide member 202 has a locking mechanism coupling end 702 at which the locking mechanism 212 is coupled. Locking mechanism coupling end 702 has three concentric ring areas 704, 706 and 708 formed thereon. The first ring area 704 has the guide slot 606 defined therein. The diameter of the first ring area 704 is slightly smaller than the diameter of the opening 415 in the locking member 410. This allows the inward extending flange 414 of the locking member 410 to slide along the first ring area 704. An extension 710 extends along the coupling end 702 between the second ring area 706 and the third ring area 708. When the locking mechanism 212 is assembled, the guide pin 418 is received in the guide slot 606. The spring 420 is provided around the second ring area 706 and is compressed between the inward extending flange 414 of the locking member 410 and the third ring area 708. The spring 420 biases the locking member 410 away from the guide member 202 along the longitudinal axis L of the shaft 204.

The guide slot 606 has an unlocking portion 712 with a retention wall 714 and a locking portion 716 with an opening 718 and walls 719. In the embodiment shown in FIG. 7, the retention wall 714 has a semi-cylindrical shape in order to make removal of the guide pin 418 from the slot easier. It should be appreciated, however, that the retention wall 418 can have a shape different from the one shown. Both the unlocking portion 712 and the locking portion 716 of the guide slot 606 extend parallel to the longitudinal axis L of the shaft 204. A transition portion 720 connects the locked portion 712 to the unlocked portion 716 of the guide slot 606.

Referring now to FIGS. 4 and 7, when the locking mechanism 212 is in the unlocked position 304, the spring 420 presses the guide pin 418 against the retention wall 714 in the unlocked portion 714 of the guide slot 606. The locking pin 416 is unable to engage the locking slot 406 in the flange 404 of retaining shaft 402, because the retention wall 714 of the guide slot 606 prevents the locking member 410 from extending towards the retention flange 404 of the retaining shaft 402. Since the locking pin 416 in the unlocked position does not engage the locking slot 406 in the retaining shaft 402, the retaining shaft 402 can freely rotate so that tool 214 is rotatable.

Figure 8:
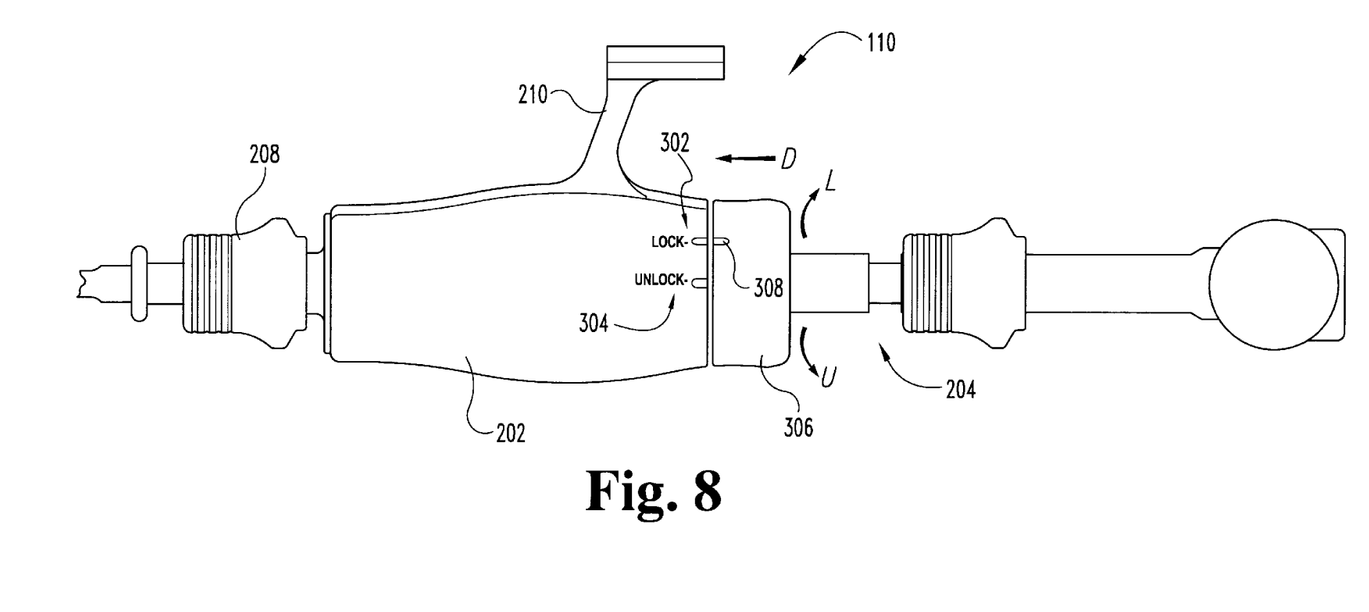
FIG. 8 is a side view of the medical instrument shown in FIG. 1 with the locking mechanism in a locked position.

To lock the shaft 204 at a specific orientation, the cover 306 is pushed in direction D towards the guide member 202, as shown in FIG. 8, and rotated in direction L until the position indicator 308 aligns with the locked indicator 302. During locking of the shaft 204, the spring 420 is compressed when the cover 306 is pushed in direction D. When the cover 306 is rotated, the guide pin 418 travels along the transition portion 420 between the unlocking portion 712 and the locking portion 716 of the guide slot 606 (FIG. 7). As soon as the guide pin 418 is in the locking portion 716 of the guide slot 606, the spring 420 is able to press the locking member 410 towards the retention flange 404 of the retaining shaft 402.

If the locking slot 406 is not aligned with the locking pin 416 when the locking mechanism 212 is moved to the locked position, the locking pin 416 will ride along the retention flange 404 until the drive shaft 204 is rotated so that the locking pin 416 engages the slot 406. This ensures that the shaft 204 can only be locked at a specified rotational orientation, and this in turn ensures that the tool 214 is only locked at this specified orientation.

Figure 9:
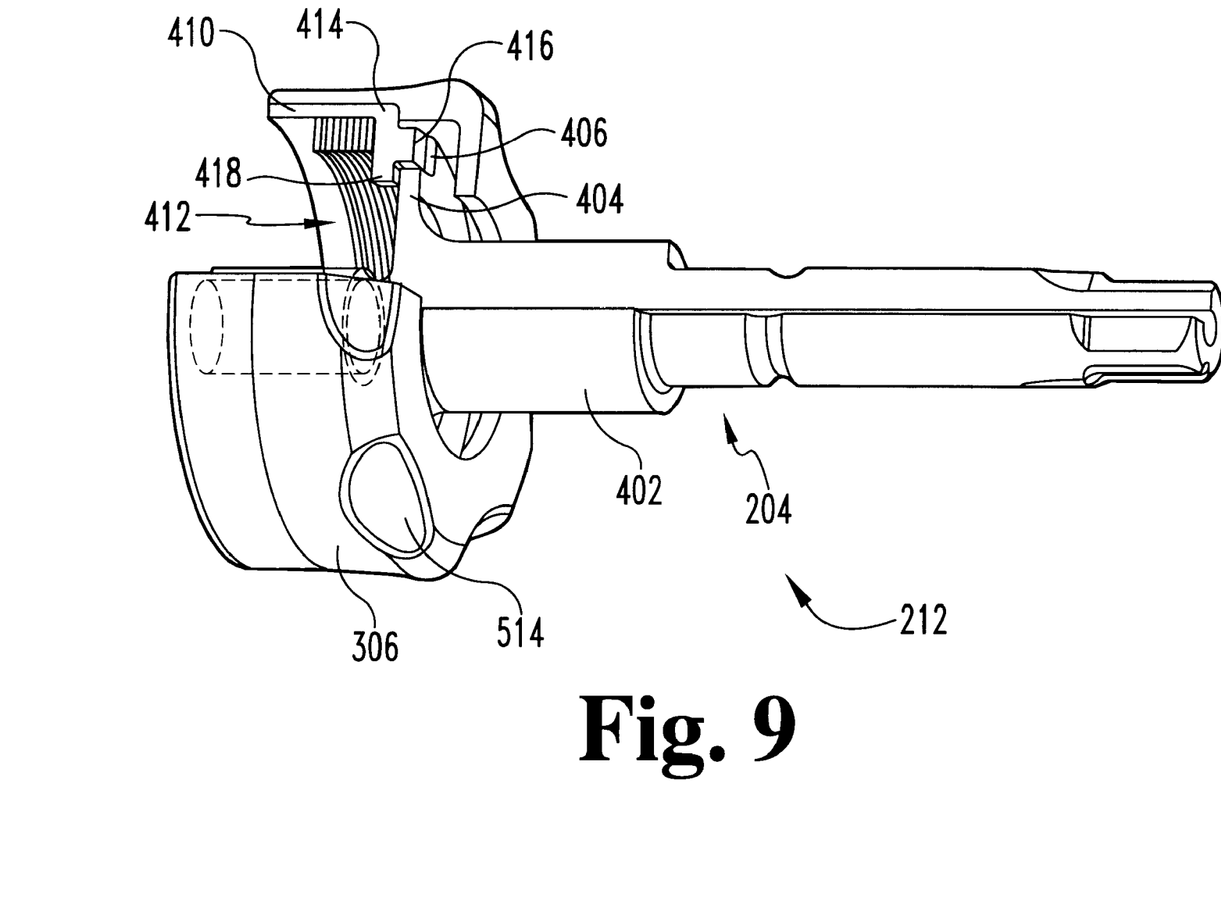
FIG. 9 is a cross-sectional perspective view of the locking mechanism in the locked position.

In the locked position, as shown in FIG. 9, the locking pin 418 engages the slot 406 in the retention flange 404. The retention flange 404 of the retaining shaft 402 abuts the inward-extending flange 414 of the locking member in order to retain the locking member 410. The walls 719 of the guide slot 606 engage to the guide pin 418 in order to prevent the locking member 410 from rotating. The locking of the guide pin 418 in the slot 406 of the drive shaft 204 prevents the shaft 204 from rotating, and this in turn prevents the tool 214 from rotating. It should be appreciated that the locking mechanism 212 can include multiple guide slots 606 and guide pins 418 in order to provide greater support for the locking member 410. As shown, the locking member 410 has a single locking pin 416 so that the rotational orientation of a tool can be determined even if the tool is rotationally asymmetrical. In the embodiment shown in FIG. 5, the locking member 410 has a second guide pin 418 that is adapted to engage a second guide slot 606.

While specific embodiments of the present invention have been shown and described in detail, the breadth and scope of the present invention should not be limited by the above described exemplary embodiments, but should be defined only in accordance with the following claims and their equivalents. All changes and modifications that come within the spirit of the invention are desired to be protected.

What is claimed is:

1. A trackable medical instrument, comprising:
   a guide member adapted to be positionally tracked by a surgical navigation system;
   an emitter array coupled to said guide member for position tracking said guide member;
   a drive shaft rotatably coupled to said guide member;
   a locking mechanism provided along said drive shaft, said locking mechanism having an unlocked position in which said drive shaft rotates relative to said guide member and a locked position in which said drive shaft is rotationally stationary relative to said guide member;
   wherein said locking mechanism includes a retaining shaft connected to said drive shaft, said retaining shaft having a retaining flange with a locking slot defined therein;
   wherein said locking mechanism includes a locking pin adapted to engage said locking slot for locking said drive shaft in a rotationally stationary condition; and
   wherein said locking mechanism includes a locking member, provided along said drive shaft between said flange and said guide member, said locking member having an inward radially extending flange with said locking pin extending from said inward extending flange and a guide pin extending from said inward extending flange, said guide member having a guide slot defined therein for guiding said guide pin.

2. The instrument of claim 1, wherein said locking mechanism includes a spring provided between said locking member and said guide member for biasing said locking member.

3. The instrument of claim 2, wherein said locking mechanism includes a cover fitted around said locking member.

4. An apparatus, comprising:
   a surgical navigation system including a sensor array for position tracking a trackabale medical instrument in a patient; and
   said trackable medical instrument including
   a guide member,
   an emitter array coupled to said guide member, said emitter array being operatively coupled to said surgical navigation system for position tracking said trackable medical instrument,
   a drive shaft rotatably coupled to said guide member,
   a tool coupled to said drive shaft, and
   a locking mechanism provided along said drive shaft, said locking mechanism having an unlocked position in which said tool rotates relative to said guide member and a locked position in which said tool is locked at a specified rotational orientation relative to said emitter array to ensure that the rotational orientation of said tool within the patient is known.

5. The apparatus of claim 4, wherein said locking mechanism. includes a cover, said cover having apposition indicator defined thereon to indicate said locked position and said unlocked position.

6. The apparatus of claim 4, wherein said drive shaft has a first end with a first coupling portion adapted to interchangeably receive a drive source for applying torque to said drive shaft, said drive shaft having a second end with a second coupling portion adapted to interchangeably receive said tool.

7. The apparatus of claim 6, wherein said first coupling portion includes a first quick connect mechanism for connecting to said drive source.

8. The apparatus of claim 7, wherein said second coupling portion includes a second quick connect mechanism for connecting to said tool.

9. The apparatus of claim 6, further comprising said drive source coupled to said first end.

10. The apparatus of claim 9, wherein said drive source includes a handle coupled to said first end.

11. The apparatus of claim 4, wherein said surgical navigation system includes:
    a processor operatively coupled to said emitter array to track said trackable. medical instrument;
    a display operatively coupled to said processor for displaying the position of said trackable medical instrument; and
    a reference array operatively coupled to said processor for generating signals representing various reference body locations of the patient.

12. A trackable medical instrument, comprising:
    a guide member adapted to be positionally tracked by a surgical navigation system;
    an emitter array coupled to said guide member for position tracking said guide member;
    a drive shaft rotatably coupled to said guide member, said drive shaft being configured to rotate a tool; and a locking mechanism provided along said drive shaft, said locking mechanism having an unlocked position in which said drive shaft rotates relative to said guide member and a locked position in which said drive shaft is locked at a specified rotational orientation relative to said emitter array to ensure that the rotational orientation of the tool is known.

13. The instrument of claim 12, wherein said locking mechanism includes a retaining shaft connected to said drive shaft, said retaining shaft having a retaining flange with a locking slot defined therein.

14. The instrument of claim 13, wherein said locking mechanism includes a locking pin adapted to engage said locking slot for locking said drive shaft in a rotationally stationary condition.

15. The instrument of claim 14, wherein said locking mechanism includes a locking member provided along said drive shaft between said flange and said guide member, said locking member having an inward radially extending flange with said locking pin extending from said inward extending flange and a guide pin extending from said inward extending flange, said guide member having a guide slot defined therein for guiding said guide pin.

16. The instrument of claim 15, wherein said locking mechanism includes a spring provided between said locking member and said guide member for biasing said locking member.

17. The instrument of claim 16, wherein said locking mechanism includes a cover fitted around said locking member.

18. The instrument of claim 12, wherein said locking mechanism includes a cover, said cover having a position indicator defined thereon to indicate said locked position and said unlocked position.

19. The instrument of claim 12, wherein said drive shaft has a first end with a first coupling portion adapted to interchangeably receive a drive source for applying torque to said drive shaft, said drive shaft having a second end with a second coupling portion adapted to interchangeably receive the tool.

* * * * *

UNITED STATES PATENT AND TRADEMARK OFFICE
CERTIFICATE OF CORRECTION

PATENT NO. : 6,556,857 B1
DATED : April 29, 2003
INVENTOR(S) : Bradley T. Estes and Douglas N. Baker It is certified that error appears in the above-identified patent and that said Letters Patent is hereby corrected as shown below:

Column 5,
Line 67, replace "member,provided" with -- member provided --.

Column 6,
Line 32, replace"nism. includes" with -- nism includes --.

Line 32, replace "apposition" with -- a position --.

Signed and Sealed this

Eleventh Day of November, 2003

JAMES E. ROGAN
*Director of the United States Patent and Trademark Office*